United States Patent [19]
Sakai et al.

[11] Patent Number: 5,102,392
[45] Date of Patent: Apr. 7, 1992

[54] AIR DETECTOR FOR USE IN INFUSION PUMP

[75] Inventors: Eiichi Sakai, Nara, Japan; George A. Bowman, Vernon Hills; Edmund D. D'Silva, Highland Park, both of Ill.

[73] Assignees: Sharp Kabushiki Kaisha, Osaka, Japan; Baxter International Inc., Deerfield, Ill.

[21] Appl. No.: 513,882

[22] Filed: Apr. 24, 1990

[30] Foreign Application Priority Data

Apr. 28, 1989 [JP] Japan ................. 1-50548[U]

[51] Int. Cl.$^5$ .............................................. A61M 1/00
[52] U.S. Cl. ........................... 604/122; 128/DIG. 13; 340/632
[58] Field of Search ............... 604/122, 123, 124, 125, 604/126; 340/632; 128/DIG. 13

[56] References Cited

U.S. PATENT DOCUMENTS

| | | | |
|---|---|---|---|
| 4,068,521 | 1/1978 | Cosentino et al. | |
| 4,312,341 | 1/1982 | Zissimopoulos et al. | 604/67 |
| 4,344,429 | 8/1982 | Gupton et al. | 604/67 |
| 4,367,736 | 1/1983 | Gupton et al. | 604/30 |
| 4,418,565 | 12/1983 | St. John | 73/19.03 |
| 4,559,454 | 12/1985 | Kramer | 604/122 |
| 4,758,228 | 7/1988 | Williams | |
| 4,764,166 | 8/1988 | Spani | 604/122 |
| 4,857,050 | 8/1989 | Lentz et al. | 604/122 |
| 4,884,065 | 11/1989 | Crouse et al. | 128/DIG. 13 |
| 4,981,467 | 1/1991 | Bobo, Jr. et al. | 604/65 |

FOREIGN PATENT DOCUMENTS

| | | | |
|---|---|---|---|
| 8201651 | 5/1982 | European Pat. Off. | |
| 0121406 | 10/1984 | European Pat. Off. | |
| 181691 | 5/1986 | European Pat. Off. | 604/122 |
| 8603571 | 6/1986 | European Pat. Off. | |
| 3034874 | 4/1982 | Fed. Rep. of Germany | 604/122 |
| 3141576 | 5/1983 | Fed. Rep. of Germany | |

*Primary Examiner*—Gene Mancene
*Assistant Examiner*—Michael Lynch

[57] ABSTRACT

An air detector according to the present invention utilizes a unitary type sensor for detecting air bubbles or columns in an infusion solution flowing through a tube. Because of a unique design for a tube-receiving groove and a cooperating abutting member, the difficulty in loading a tube heretofore encountered with the use of unitary type sensor is obviated. Thus, the tube can be loaded in the air detector easily with good reliability.

9 Claims, 3 Drawing Sheets

AIR DETECTOR FOR USE IN INFUSION PUMP

BACKGROUND OF THE INVENTION

1. Field of the Invention

The present invention generally relates to an air detector for use in an infusion device, and more particularly, to an air detector designed to detect air bubbles or columns in an infusion solution flowing through a tube from a supply bag, etc. into a human body in the medical infusion device or the like, which facilitates easy and reliable loading of said tube into the infusion device.

2. Description of the Prior Art

Prior art infusion devices of the kind referred to above include an air detector using a ultrasonic or an optical sensor for detecting air bubbles or columns in the liquid flowing through a tube. The air detector is loaded in a part of the tube.

Two types of the air detectors are known. More specifically, in the separate type as shown in FIG. 5, a signal emitting member 1 and a signal receiving member 3 of the sensor are separate components in such structure that the former is mounted on a stationary unit 2 of a pumping station, while the latter is carried by a movable unit 4 such as a door. When the door 4 is closed, a channel 6 is defined between an upper surface of the signal emitting member 1 of the stationary unit 2 and a lower surface of the signal receiving member 3 of the movable unit 4, into which a tube 5 is accommodated. Accordingly, when the movable unit 4 is closed while the tube 5 is loaded into an upper recess 7 defined in the signal emitting member 1 of the unit 2, the tube 5 is deformed into a flattened configuration within the channel 6 to provide an enlarged surface area 5a to be in contact with the signal emitting and receiving members 1 and 3.

On the other hand, in the unitary type of the air detector as shown in FIGS. 6 and 7, a tube-receiving groove 8 is defined in the stationary unit 2. Both the signal emitting and receiving members 1 and 3 are embedded in the opposing walls of the groove 8. The unitary type is mainly used for detecting relatively short air bubbles or columns and therefore the length of tube-receiving groove 8 is relatively short, exerting less resistance in contact between the groove and the tube. Accordingly, the tube may be fitted into the groove 8 by pushing by fingers.

In the above-described separate type, it is difficult to maintain a constant distance between the signal emitting and receiving members so as to stabilize the performance of the detector.

In the unitary type, it is necessary for the tube-receiving groove 8 to have a relatively narrow width in order to obtain a high sensitivity in the detector. In order that relatively elongated air bubbles or columns can be detected in the narrow groove 8, it is necessary to correspondingly elongate the inter-sensor distance in a lengthwise direction of the tube as indicated in FIG. 7. This necessarily increases the frictional resistance of the groove and makes it difficult to place the tube in the groove. In other words, when the air bubbles or columns of a size corresponding to L1 are to be detected, the inter-sensor distance between sensors 1 and 1, and 3 and 3 is necessary to be L1 as shown in FIG. 6. Meanwhile, when the air columns of a size corresponding to L2 are to be detected, the inter-sensor distance should be set L2 as shown in FIG. 7.

SUMMARY OF THE INVENTION

Accordingly, the present invention has been devised with a view to substantially solve the above-described problems inherent in the prior art, and has for its essential object to provide an air detector which utilizes a unitary type sensor assuring a constant distance between signal emitting and receiving members and correspondingly a stable detecting efficiency. The conventional difficulty in loading a tube encountered with the use of unitary type sensor is obviated by employing a unique design for a tube-receiving groove, whereby elongated air bubbles or columns can be detected.

In accomplishing the above-described object, according to the present invention, an air detector is provided which is designed to detect air bubbles or columns in an infusion solution flowing through a tube loaded in a pumping station. The tube extends from a supply bag, etc. to a patient through the detector between a signal emitting member and a signal receiving member thereof. The detector of the present invention is characterized in that the tube is fitted into a groove defined in a stationary unit of the pumping station, the groove having a tube-fixing section of a width narrower than the outer diameter of the tube defined at the lower side of the groove, the signal emitting member and the signal receiving member being disposed on the opposing side walls of the tube-fixing section, the upper section of the groove being defined by one side wall which flares outwardly from the tube-fixing section and the other side wall which is perpendicular and continues to the tube-fixing section. The detector is further characterized in that a tube-abutting member is provided on a movable unit rotating to the stationary unit such as a door whereby the tube is pushed into the groove and further into the tube-fixing section by the tube-abutting member when the door is closed while the dislodgement of the tube from the groove is prevented.

Accordingly, since the present invention utilizes a unitary type sensor which is stable in the detecting accuracy, and the difficulty in loading a tube conventionally encountered with the use of unitary type sensor is obviated by the tube-abutting member provided in the movable unit, the tube is easily loaded into the detector by forcible pushing of the tube with the tube abutting-member.

BRIEF DESCRIPTION OF THE DRAWINGS

This and other objects and features of the present invention will become apparent from the following description taken in conjunction with one preferred embodiment thereof with reference to the accompanying drawings, in which.

DETAILED DESCRIPTION OF THE INVENTION

Figure 1:
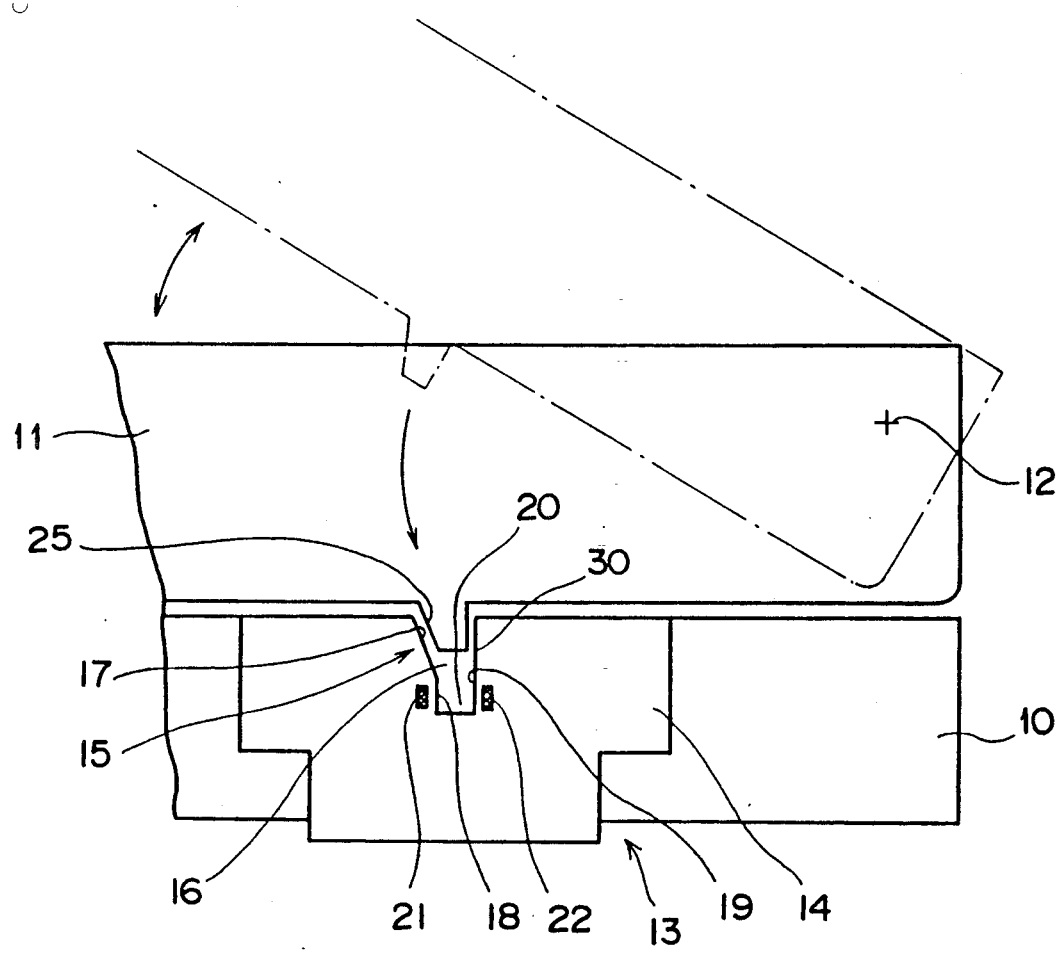
FIG. 1 is a schematic front elevational view of an air detector according to a preferred embodiment of the present invention.
Figure 2:
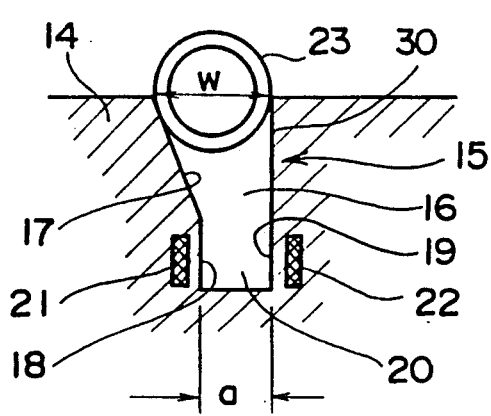
FIGS. 2 and 3 are cross sectional views showing the loading process of a tube.
Figure 3:
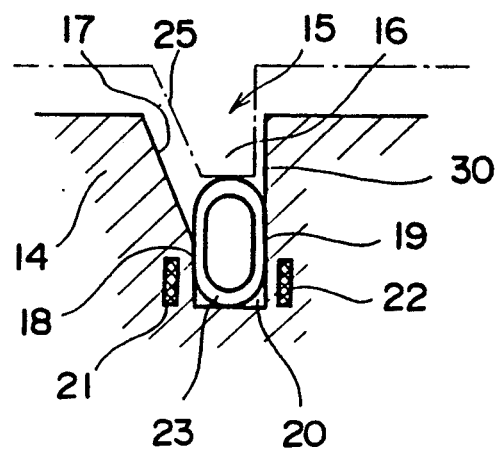

Before the description of the present invention proceeds, it is to be noted here that like parts are designated by like reference numerals throughout the accompanying drawings.

A preferred embodiment of the present invention will be described in detail with reference to the accompanying drawings.

Referring to FIG. 1, an air detector according to the preferred embodiment of the present invention shown therein consists of a stationary unit 10 of an infusion device and a movable unit 11, i.e., a door of the pump. The door 11 is pivotable about its axis 12 in a direction indicated by an arrow to close and open the stationary unit 10. A body 14 formed of synthetic resin of an air detector generally indicated at 13 is embedded in the stationary unit 10. The body 14 defines a groove 15 opening upwards for receiving a tube. As shown in FIG. 1, the groove 15 has an upper section 16 thereof defined by two side walls, one of which 17 is flared outwardly and the other of which 30 extends in a plane perpendicular to the upper surface of the stationary unit 10. The groove 15 further defines a tube-fixing section 20 adjacent its base defined by opposing side walls 18, 19 which extend in parallel to each other and perpendicularly to the tube-fixing section 20. The side wall 19 is flush with the side wall 30 of the upper section 16. Therefore, the tube-fixing section 20 has rectangular cross section. A signal emitting member 21 and a signal receiving member 22 of an ultrasonic sensor are embedded within the body 14 adjacent the side walls 18 and 19, respectively.

The width a of the tube-fixing section 20 is set smaller than the outer diameter w of a tube 23 to be inserted in the groove 15 (a<w). This provides a large contact area between the tube 23 and the side walls 18, 19 respectively provided with signal emitting and signal receiving members of the sensor as desired for detecting air bubbles or columns passing through the tube 23. The tube 23 is fitted within the tube-fixing section 20 of the small width a along the outwardly flared outer section 16. Thus, the tube 23 is deformed from a circular configuration into an oval configuration in cross section.

As discussed above, in order to detect a relatively long air bubbles or columns, it is required to extend the inter-sensor distance (in an axial direction of the tube) thereby making it necessary for the tube-receiving groove 15 to have a corresponding extended length. Thus, the length of the groove 15 in this embodiment is rendered considerably longer than that of the conventional design of unitary type in proportion to the length of air bubbles or columns to be detected. However, the use of an elongated groove 15 may develop a problem of difficulty in loading of the tube 23 in the fixing section 20 because of the increased resistance in contact between the outer wall of the tube 23 and the inner wall of the groove.

Figure 4:
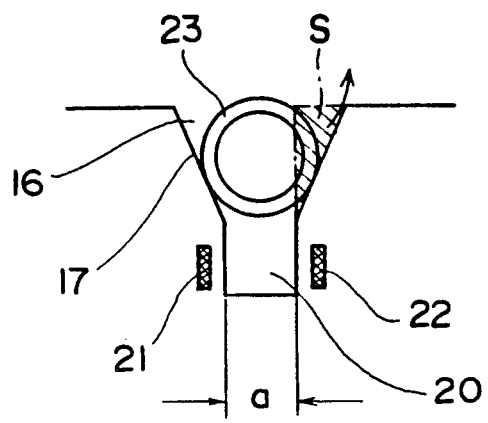
FIG. 4 is a cross sectional view explanatory of a problem in loading the tube.
Figure 5:
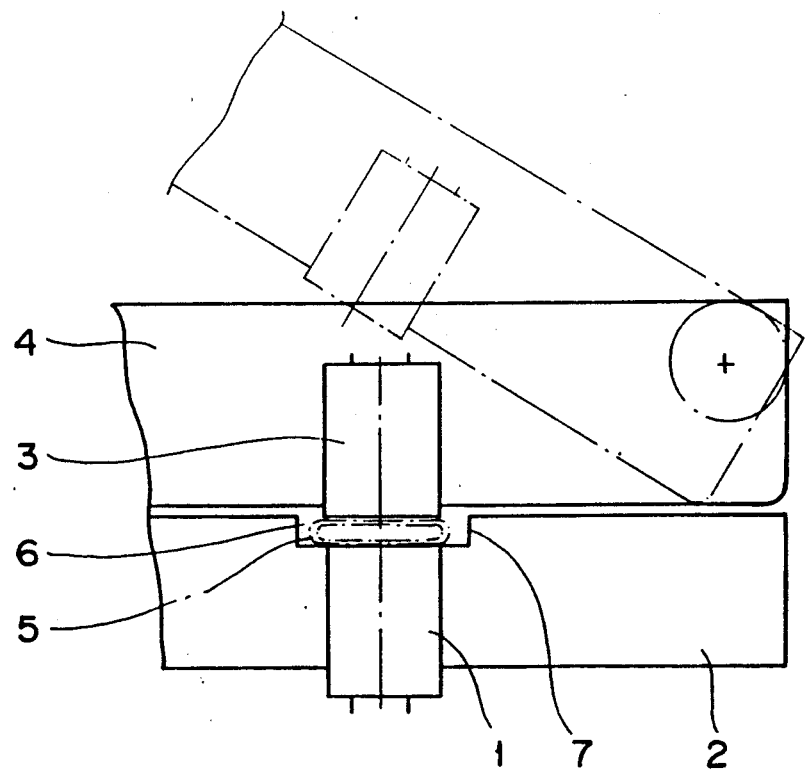
FIG. 5 is a schematic front elevational view of a prior art air detector of the separate type.
Figure 6:
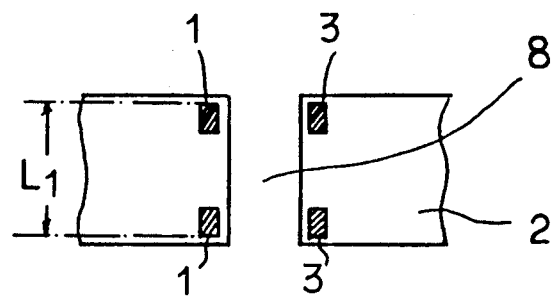
FIGS. 6 and 7 are schematic views of a prior art air detector of the unitary type.
Figure 7:
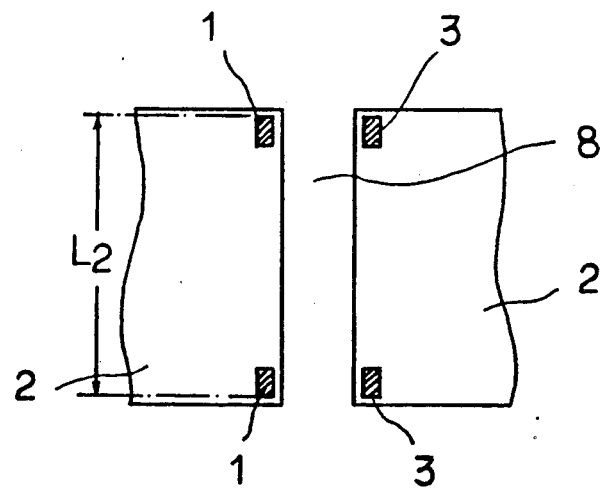

In order to obviate the above problem, according to the present invention, a tube-abutting member 25 is provided on the lower surface of the door 11 corresponding to the position where the tube 23 is pushed into the tube-fixing section 20 in the groove 15. The abutting member 25 has a configuration complementary to, but smaller than the upper section 16. In other words, one of the side walls of the abutting member 25 flares outwardly, while the other projects at right angles to the movable unit 11. When the door 11 is pivoted about its axis 12, the abutting member 25 is inserted into the groove 15 from above while exerting a clockwise force on the tube 23. On the contrary, if the side walls 17 and 30 in the upper section 16 of the groove 15 are both notched and sloped outwardly as indicated by a hatch S in FIG. 4, the tube 23 would stably rest on the upper section 16. However, when the tube 23 is pushed by the projecting abutting member 25 into the fixing section, the tube 23 would be dislodged from the groove 15 as shown by an arrow in FIG. 4. This rotational or rolling displacement of the tube 23 may be prevented by making the side wall 19 of the upper section 16 in the groove 15 flush with the side wall 30 thereby to push the tube 23 forcibly in the fixing section 20 by the abutting member 25.

Consequently, in the above-described structure, the tube 23 may be simply loaded in position of the air detector 13 by placing it first in the upper section 16 of the groove 15 and then closing the door 11. In other words, when the door 11 is closed, the tube-abutting member 25 enters the groove 15, forcing the tube 23 from the upper section 16 into the tube fixing section 20. This process allows the tube to be fitted into the fixing section 20 in an automatic and reliable fashion even if a large frictional resistance is encountered between the outer surface of the tube 23 and the inner surface of the groove 15.

As will be clear from the foregoing description, according to the present invention, the air detector utilizes the sensor of unitary type with the signal emitting and receiving members embedded in the opposing side walls defining the tube-receiving groove formed in the stationary unit. Once the tube has been loaded in the tube fixing section in the groove, the tube can be placed in constant position to the sensor, namely, between the opposing signal emitting and receiving members spaced a constant distance, making it possible to obtain a stable and reliable performance in the air detector. Furthermore, since the abutting member carried by the door assists the loading of the tube into the fixing section, the tube may be easily inserted even into a relatively long groove. This permits for the detector to detect air bubbles or columns of various sizes without developing any difficulty in loading the tube into the detector. Moreover, the use of unitary type sensor having both the signal emitting and receiving members mounted in the stationary unit is advantageous because it does not require recalibration of the relative distance between the signal emitting and receiving members in order to stabilize its air detecting performance.

What is claimed is:

1. In an air detector for detecting air bubbles or columns in an infusion solution flowing through a tube located in a pumping station, the tube extending from a supply bag of the infusion solution to a patient through the detector between a signal emitting member and a signal receiving member the air detector comprising:

a stationary unit of the pumping station including;
   a groove including a base and two side walls for receiving the tube;
   an upper section of the groove being defined by a first side wall which flares outwardly from a tube-fixing section and a second side wall which is perpendicular to the base of the groove along its length in the tube-fixing section; and
   a movable unit in pivoting relation to said stationary unit of the pumping station; and a tube-abutting member movable into said groove when said movable unit is closed, whereby when said tube is pushed into said tube fixing section from the upper section by said tube abutting member, dislodgement of said tube from said groove is prevented by said second side wall.

2. The air detector according to claim 1, further comprising;

the tube-fixing section having a width narrower than the outer diameter of said tube defined adjacent the base of said groove.

3. The air detector according to claim 1, further comprising;

the signal emitting member and the signal receiving member disposed on the side walls of said tube-fixing section, the side walls being located opposite to each other.

4. An apparatus for detecting air bubbles in a liquid flowing through a tube comprising:

a stationary unit containing a groove that includes a base and a first and second oppositely located side walls;

said first wall including an upper section that flares outwardly from the groove;

said second wall being substantially perpendicular to said base along its entire length;

a movable member including means for pivoting toward said stationary unit; and a signal emitting member and a signal receiving member located opposite to each other in the groove; and a tube-abutting member operatively connected to said movable member, and movable into said groove, so that when the tube is pushed into said groove by the tube abutting member, dislodgement of the tube from said groove is prevented by said second side wall.

5. The apparatus as claimed in claim 4, wherein said movable member is a door.

6. The apparatus as claimed in claim 4, wherein said groove has a width adjacent the base which is narrower than the outer diameter of the tube.

7. The apparatus as claimed in claim 4, wherein said signal emitting member is located in one of said side walls; and said signal receiving member is located in the other of said side walls.

8. An apparatus for detecting air bubbles in liquid flowing through a tube comprising:

a groove for receiving said tube, said groove including a base and two side walls oppositely positioned to each other;

one of the side walls including a flared out top portion, the other of said side walls being substantially perpendicular to said base from substantially along the entire length of the wall; and a movable member including a tube-abutting member sized to fit into the groove so that when the tube is pushed into the groove by the tube-abutting member dislodgement of the tube is prevented; and a signal emitting member and a signal receiving member located opposite to each other in the groove.

9. The apparatus as claimed in claim 8, wherein one side wall includes said signal emitting member and the other side wall includes said signal receiving member.

* * * * *